(12) United States Patent
Bortolotti

(10) Patent No.: US 6,315,555 B1
(45) Date of Patent: Nov. 13, 2001

(54) SERIES OF SINGLE-USE PRINT HOLDERS FOR EDENTULOUS PATIENTS AND METHOD FOR THE REALIZATION OF TOTAL PROSTHESES

(76) Inventor: Lilia Bortolotti, Via Riva di Reno, 56, 40122 Bologna (IT)

( * ) Notice: Subject to any disclaimer, the term of this patent is extended or adjusted under 35 U.S.C. 154(b) by 0 days.

(21) Appl. No.: 09/762,686

(22) PCT Filed: Aug. 5, 1999

(86) PCT No.: PCT/IB99/01387

§ 371 Date: Feb. 12, 2001

§ 102(e) Date: Feb. 12, 2001

(87) PCT Pub. No.: WO00/09035

PCT Pub. Date: Feb. 24, 2000

(30) Foreign Application Priority Data

Aug. 11, 1998 (IT) .............................................. BO98A0492

(51) Int. Cl.[7] ....................................................... A61C 9/00
(52) U.S. Cl. ................................................. 433/37; 433/41
(58) Field of Search ................................ 433/37, 38, 41, 433/43, 48

(56) References Cited

U.S. PATENT DOCUMENTS 3,473,225 * 10/1969 Deuschle et al. .
4,227,877 10/1980 Tureaud et al. .

FOREIGN PATENT DOCUMENTS 855148 9/1960 (GB) .

* cited by examiner

*Primary Examiner*—Ralph A. Lewis
(74) *Attorney, Agent, or Firm*—Young & Thompson

(57) ABSTRACT

The invention relates to a series of single use print holders for obtaining prints of the maxillary arch and of the mandibular arch in edentulous patients; on the periphery the print holders (1;16) comprise a channel (4;17) which surrounds the gingival crest maintaining a certain gap between the surface of the print holder (1;16) and the surface of the gum for the material for obtaining the prints; to favor stability, the print holder is provided with gingival supports (11,12;25,32) and for better positioning it comprises a frond handle (14;32) and projections (33); by selecting a suitably sized print holder (1;16) among the ones in the series, the final print to realize the total prosthesis can be obtained directly without making the preliminary primary print.

8 Claims, 3 Drawing Sheets

SERIES OF SINGLE-USE PRINT HOLDERS FOR EDENTULOUS PATIENTS AND METHOD FOR THE REALIZATION OF TOTAL PROSTHESES

TECHNICAL FIELD

The present invention relates to a series of single use print holders for obtaining prints of the maxillary arch and of the mandibular arch in edentulous patients and to the method for the realisation of total prostheses.

In particular, the present invention relates to a series of single use print holders that are used in the realization of total prostheses of the maxillary arch and of the mandibular arch, prostheses which may be both of the type without fastening points and with natural or artificial fastening points. The present invention also relates to the method for the realization of total prostheses of the maxillary arch and of the mandibular arch.

THE BACKGROUND ART

The current art for obtaining a total prostheses for the maxillary arch or for the mandibular arch essentially comprises four phases that precede the actual construction phase of the prosthesis.

The first phase entails obtaining a negative primary print of the edentulous arch to be fitted with a prosthesis. For this phase, a standard print holder is used, which is available in different sizes and coarsely fits on the arch to be provided with a prosthesis. The print holder is filled with suitable material, for instance alginate, it is positioned on the arch and the so-called negative primary print of the arch is obtained.

In the course of the second phase, a primary model of the edentulous arch is obtained. The negative primary print of the arch is filled with appropriate material, for instance plaster, and after it has dried the so-called positive primary print of the arch is realised.

From the third phase, an individual negative secondary print holder is obtained. This print holder is individual because it is specific and personalized for the patient. On the positive primary model of the arch some preparatory interventions are performed, such as contouring the primary model, in order to obtain an individual print holder that takes into account the anatomic specificity of each individual patient.

Upon completion of these preparatory interventions the positive primary model of the arch is coated with suitable dental material, generally waxy material, to create a certain thickness with respect to the arch, and subsequently it is coated with other dental material, generally acrylic resin. When the resin is polymerised the positive primary model is removed and a negative print of the arch is obtained, which constitutes an individual secondary print holder of the arch.

The fourth phase allows to obtain a final positive model of the arch whereon the prosthesis is to be constructed.

The secondary individual print holder is subjected to border moulding, i.e. the rim of the individual print holder is coated with essentially resinous and/or waxy material, and the print holder thus coated is inserted on the arch to be fitted with a prosthesis in the mouth of the patient, who is requested to perform the functional movements that leave trace on the part of the rim of the print holder whereon material has been placed which, having certain malleability characteristics, records aggregations, separations projections etc., due to the movement of the muscles of the patient's mouth. Upon completion of this operation the individual print completed by the border moulding is "cleaned" and different dental material, for instance polysulphur, is inserted which, adhering to the negative of the individual print holder generates the negative of the individual secondary print. Then, with special dental material, generally high precision plaster, the positive and definitive secondary model that serves as the base for the realization of the prosthesis is realized.

Hence, the traditional procedure is long and relatively costly in that it entails obtaining the prints of the arches twice and it generally calls for the realization of an individual print holder in the laboratory. Moreover, obtaining the primary prints with standard print holders may cause discomfort to the patient.

DISCLOSURE OF INVENTION

To overcome such drawbacks, print holders able to be modelled have been proposed, made of metal or thermoplastic resins, or with special pastes which modelled on the arch to be fitted with a prosthesis, once hardened, obtained an individual print holder. These solutions, however, were not found valid due to problems with shape stability and excessive cost.

The purpose of the present invention is to eliminate the aforementioned drawbacks, providing a series of single use individual print holders.

The invention, as it is characterised by the independent claims, solves the problem of obtaining the prints of arches in edentulous patients with a series of print holders, already made in different sizes, which allow directly to obtain the model of the final print which serves as a basis for realising the final prostheses.

According to a preferred embodiment of the present invention, the print holders are a series of four print holders of different sizes for maxillary arches, and a series of five print holders of different sizes for mandibular arches.

The dependent claims refer to preferred embodiments of the present invention.

One of the advantages obtained by means of the present invention essentially consists of the fact that it is simple and its realisation is relatively inexpensive and that it allows to shorten the method for obtaining total prostheses.

The technical features and advantages of the invention shall be made more readily apparent from the detailed description that follows, made with reference to the accompanying drawings, which represent an embodiment provided purely by way of non limiting example.

DESCRIPTION OF THE ILLUSTRATIVE EMBODIMENT

For the description that follows reference is made to a maxillary print holder and a mandibular print holder, both of intermediate size among those that constitute the series of the present invention. All maxillary and mandibular print holders of the series have substantially similar shapes, with only the dimensions varying, so the description that follows does not lose its general nature.

In accordance with FIGS. 1 through 5, the number 1 indicates a print holder for the maxillary arch. This print holder is a sample of the series of maxillary print holders constituting the subject of the present invention.

The print holder 1 is so shaped in its three dimensions as to adapt itself to the anatomy of the maxillary arch contouring the edentulous crest.

Figure 1:
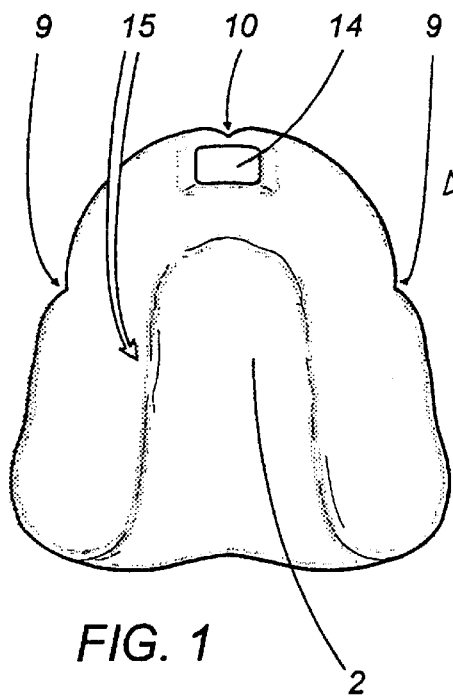
FIG. 1 shows a front view, outer side of a print holder for the maxillary arch realised in accordance with the present invention and comprised in the series of print holders of the present invention.
Figure 2:
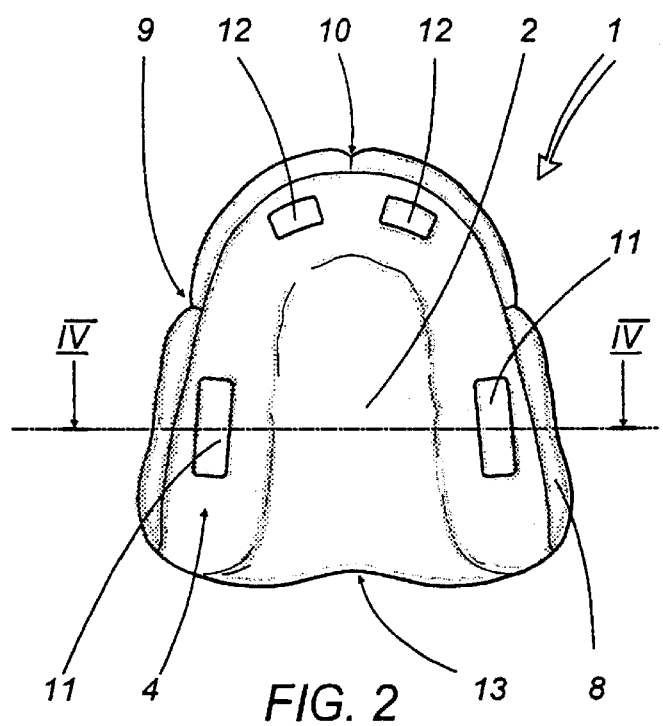
FIG. 2 shows a front view, inner side of the print holder for the maxillary arch as per FIG. 1.
Figure 3:
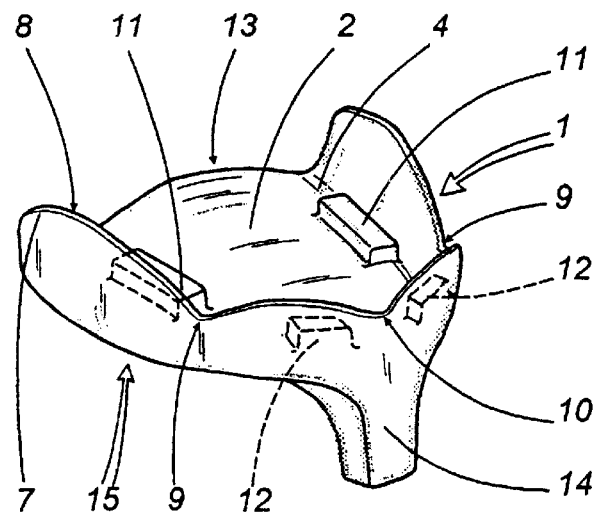
FIG. 3 shows a perspective view of the print holder for the maxillary arch as per FIG. 1.
Figure 4:
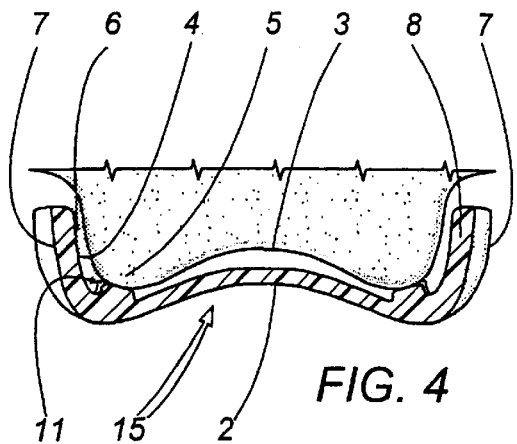
FIG. 4 shows a section view, according to line IV—IV of FIG. 2, of the print holder for the maxillary arch as per the previous figures.
Figure 5:
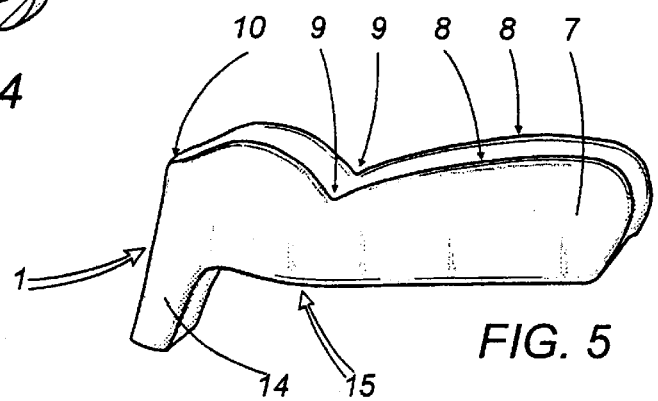
FIG. 5 shows a perspective side view of the print holder for the maxillary arch as per the previous figures.
Figure 6:
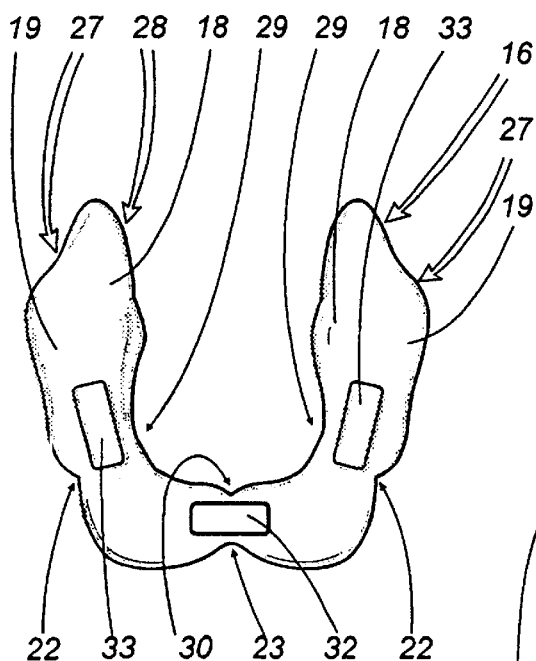
FIG. 6 shows a front view, outer side of a print holder for the mandibular arch obtained in accordance with the present invention and comprised in the series of print holders of the present invention.
Figure 7:
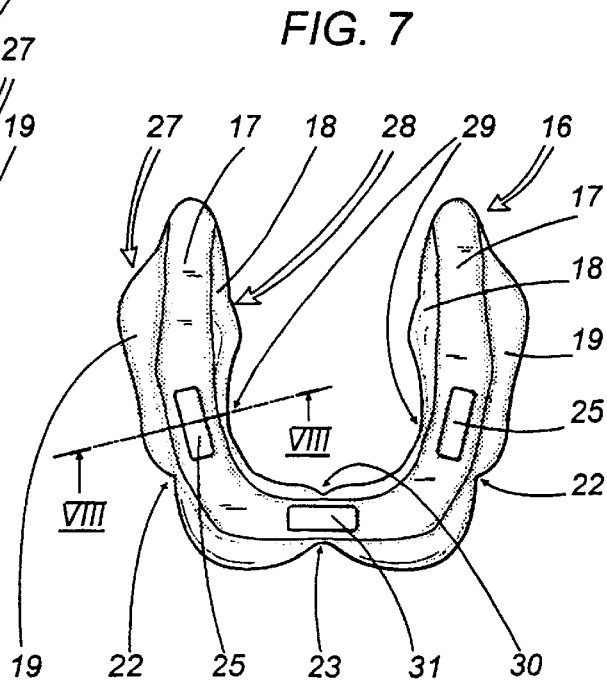
FIG. 7 shows a front view, inner side of the print holder for the mandibular arch as per FIG. 6.
Figure 8:
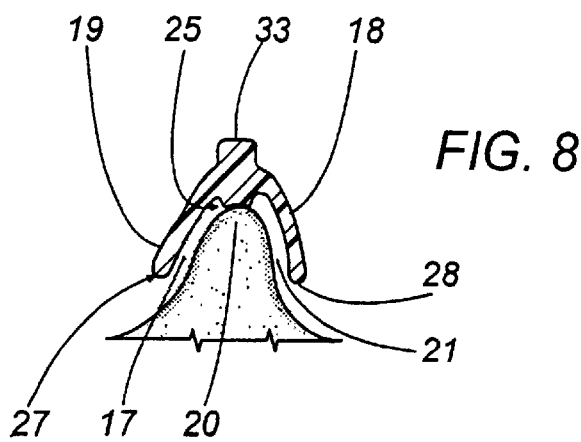
FIG. 8 shows a section view, according to line VIII—VIII of FIG. 7, of the print holder for the mandibular arch as per FIGS. 6 and 7.
Figure 9:
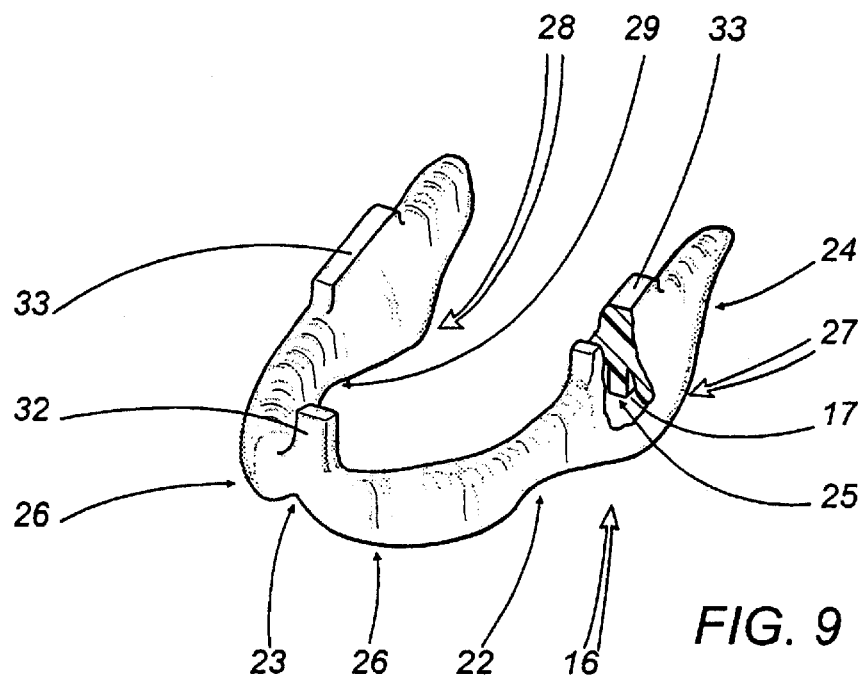
FIG. 9 shows a perspective view, with a partially sectioned part, of the print holder for the mandibular arch as per FIGS. 6 through 8.
Figure 10:
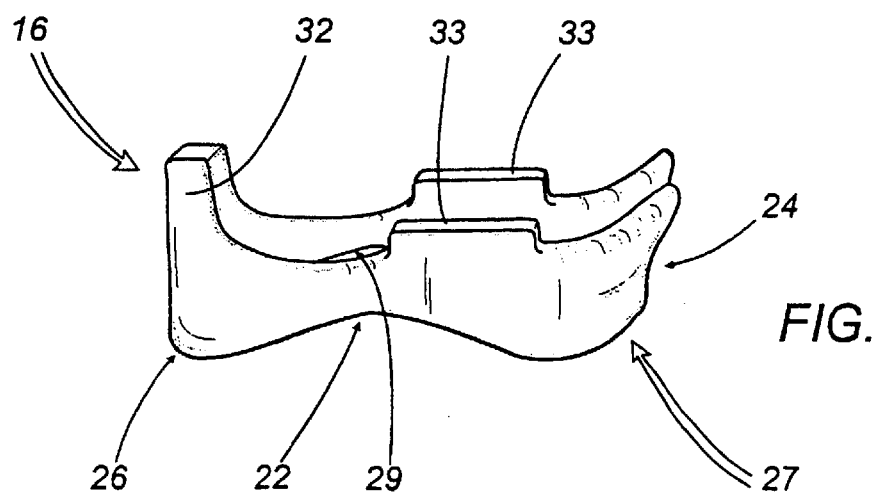
FIG. 10 shows a perspective side view of the print holder for the mandibular arch as per FIGS. 6 through 9.

The print holder 1 comprises a central vault 2 of medium convexity corresponding to the patient's palatine vault 3 (see FIG. 4). The convexity of the central vault 2 need not exactly correspond to the convexity of the patient's palatine vault 3 because the material for obtaining the prints, with which the print holder 1 is subsequently to be filled, allows to reach relatively large thicknesses without stability problems.

The vault 2 is surrounded by a channel 4 with approximately U-shaped cross section, presenting a concave surface. When the print holder 1 is positioned on the maxillary arch the channel 4 surround the gingival crest 5 (see FIG. 4) maintaining a certain gap 6 between the surface of the print holder 1 and of the gum for the material (not shown) for obtaining the prints.

The border of the outer lateral wall 7 of channel 4 presents an undulated shape which covers the tissues and corresponding projections of the lateral part of the gingival crest 5 and comprises in particular two lateral incisions 9, between the third and the fifth tooth, each in correspondence with the lateral vestibular frenulum (not shown) and a central incisions 10 in correspondence with the central frenulum (not shown). The rear part of the vault 2 is limited to the rear by a substantially straight border 13 provided with a slight convexity towards the palatine vault 3 of the patient. The border 13 extends to the limit between the hard and the soft palate (not shown).

The channel 4 is provided with two rear tissue supports 11 positioned in correspondence with the area of the first upper molar and with two front paracentral tissue supports 12 positioned in correspondence with the area of the lateral incisors. The supports 11, 12 are raised areas of the concave surface of the channel 4 and they bear down on the gums allowing to create the gap 6 with suitable thickness for the material destined to obtain the prints. The supports 11, 12 also provide an adequate support for the print holder 1 and they prevent the print holder 1 from swivelling and moving when it is positioned on the patient.

To favor the border moulding and the positioning on the maxillary arch, the print holder 1 is provided with a straight handle 14 positioned forward centrally on the outer wall 15 of the print holder 1, i.e. on the wall opposite to the one oriented towards the patient's palatine vault.

FIGS. 6 through 10 show a print holder 16 relating to the mandibular arch. This print holder is a sample of the series of mandibular print holders that constitute the subject of the present invention.

The print holder 16 is also shaped in the three dimensions in such a way as to adapt itself to the anatomy of the mandibular arch contouring the edentulous crest.

The print holder 16, seen in plan view, has a substantially horseshoe shape and comprises a channel 17, which has an approximately U-shaped cross section and presents a concave surface. The channel 17 is delimited by a lingual wall 18 situated on the inner side of the horseshoe and destined to be positioned in proximity to the tongue (not shown) and by a labial wall 19 destined to be positioned in proximity to the lower lip and to the cheek (not shown). When the print holder 16 is positioned on the mandibular arch, the channel 17 surrounds the gingival crest 20 (see FIG. 8) maintaining a certain gap 21 between the surface of the print holder 16 and the surface of the gum for the material (not shown) for obtaining the prints.

In this case as well the print holder 16, in a manner similar to the maxillary print holder 1, presents on the border 27 of the labial wall 19 of the channel 17 some lateral elevations 22, in the region between the third and the fifth tooth for the lateral vestibular frenulum (not shown), and a central incision 23 in correspondence with the central frenulum (not shown). To the side of the central incision 23, the border 27 presents two curvatures 26 for the chin's tuberosities.

In the rear-lateral external part (i.e. from the side opposite to the tongue), the print holder 16, immediately to the side of the retromolar pad (not shown), present a recess 24 shaped as an inverted and elongated S to provide some space or the front margin of the masseter muscle (not shown). The retromolar pad is therefore only partially covered because, according to the most recent orientations in the field, the prosthesis that is realised with such prints should not involve such areas.

The inner border 28 of the lingual wall 18 presents two incisions 29 situated between the fourth and fifth tooth for the mylohyoideous muscle (not shown). To the rear of the incisions 29, the border 28 overtakes the retro-mylohyoideous fossa and the retro-mylohyoideous crest (not shown) and forward it remains above the geniel tubercles (not shown) because to these tubercles are attached the muscles that move the tongue, and thus if the prosthesis involved this area as well, it could be moved by these muscles. In the rear area, the lingual wall 18 is more extended than the labial wall 19. Forward, the border 28 presents an incision 30 for the lingual frenulum (not shown). In this area as well, the lingual wall 18 is sufficiently extended for the genioglossus and geniohyoideous muscles (not shown) insert themselves very low and hence they are unlikely to be intercepted by the border of the prosthesis to be obtained from these prints.

The channel 17 is provided with two rear tissue supports 25 situated in the region of the premolars-molars and a front central tissue support 31. The supports 25, 31 are raised areas of the concave surface of the channel 17 and allow a suitable thickness of the material for obtaining prints. In this case as well, the supports 25, 31 provide a suitable support for the print holder and prevent the print holder 16 from swivelling and moving when it is positioned on the patient and the movements of the muscles of the mouth are recorded.

To favour the positioning process, the print holder 16 is provided with a straight handle 32 situated centrally and forward, and it is fitted with two projections 33 that serve to hold the print holder still during the border moulding.

The print holders are made of rigid plastic material that can be machined with normal laboratory mills, eliminating any excess material, the better to adapt it to the patient's anatomical characteristics. The material for the print holders of the present invention presents favorable ductility and malleability characteristics and is also suitable for treating patients with natural or artificial fastening points.

According to a preferred embodiment, the material used for the print holder is cold-polymerised polymethylmetacrylate.

The series of print holder comprises a certain number of print holder of different sizes for the maxillary arch, preferably four, and a certain number of print holders of different sizes for the mandibular arch, preferably five. Tests conducted by the Applicant have shown that this number of print holder is sufficient to cover the entire range of possible shapes and sizes of the maxillary and mandibular arches.

In use, a print holder is selected that is suitably sized for the maxillary or mandibular arch referring to some characteristic measure, such as the distance between the retromolar pads. The operator verifies that the print holder is suited to the arch to be modelled, possibly removing any excess parts from the print holder by machining it with the usual laboratory mills. The phase that follows is the border moulding, i.e. recording all the movements of the muscles of the patient's mouth that leave a trace on the part of the rim of the print holder. During this phase, support to the print holder is provided by the supports 11, 12 or 25, 31 that are in the channel of the print holder. Subsequently, the print holder is filled with material suitable for the final definition of the print, support to the print holder being provided now by the rim that bears on the gum.

From the definitive negative print, a positive final model of the arch to be provided with a prosthesis can be realised. For this purpose, a special dental material is used (generally, precision plaster). The positive print thus obtained is coated with resin: for the mandibular arch only on the gingival crest, for the maxillary arch also in the palatine vault area. This resin constitutes the reference base on which the artificial set of teeth is to be applied.

To apply the set of teeth, waxy material is added only to the crest area, and the waxy material positioned on the crests is then gradually replaced with artificial teeth, thereby obtaining the definitive total prosthesis.

What is claimed is:

1. Series of single use maxillary print holders for realizing directly final prints of the maxillary arch around the gingival crest (5) of edentulous patients, each maxillary print holder (1) comprising:
    a central vault (2) of intermediate convexity corresponding to the patient's palatine vault (3);
    a channel (4) that surrounds the vault (2) having an approximately U shaped cross section and presenting a concave surface, the channel (4) being delimited by an external lateral wall(7);
    a border (8) of the external lateral wall (7) having an undulated shape that covers the tissues and corresponding projections of the lateral part of the gingival crest (5), and being provided with two lateral incisions (9), between the third and the fifth tooth, each in correspondence with the lateral vestibular frenulum, a central incision (10), in correspondence with the central frenulum;
    a border (13) delimiting the rear part of the print holder (1), the border (13) being substantially straight and provided with a slight convexity towards the patient's palatine vault (3), the border (13) extending to the limit between the hard and the soft palate
    characterized in that,
        the channel (4) is provided with two rear tissue supports (11) situated in correspondence with the area of the first upper molar and with two front paracentral tissue supports (12) situated in correspondence with the area of the lateral incisors, the supports (11,12) having a large bearing surface and being raised areas of the concave surface of the channel (4) that bear down on patient's gums, provide an adequate support preventing the print holder (1) from swivelling and moving when it is positioned on the patient and create a gap (6) of a thickness suited to the material for obtaining the prints, and in that the maxillary print holder is made of cold-polymerised polymethylmetacrylate, a rigid plastic material machinable with laboratory mills for eliminating any excess material for adapting the print holder to the patient's anatomical characteristics.

2. Series of print holders according to claim 1, characterized in that in order to favor its functionality and positioning on the maxillary arch, each print holder (1) is provided with a straight handle (14) situated centrally in the front.

3. Method for realizing total prostheses of the maxillary arch and of the mandibular arch using the series of print holders to directly obtain final prints according to claim 1, characterized in that it comprises the following phases:
    selecting a print holder (1;16) of a size suited for the maxillary or mandibular arch referring to some characteristic measurements, such as the distance between the retromolar pads,
    performing the border moulding process, i.e. recording all the movements of the muscles of the patient's mouth that leave a trace on the rim part of the print holder;
    filling the print holder (1;16) with suitable material for the final definition of the print;
    directly realizing a positive final model of the arch to be fitted with a prosthesis, using appropriate dental material;
    coating the positive final model thus obtained with resin, to constitute the reference base on which the artificial set of teeth is to be applied;
    applying the artificial set of teeth on the reference base obtained in the previous phase.

4. Method according to claim 3, characterized in that the phase of filling the print holder is preceded by the removal of parts of the print holder that are in excess with respect to the patient's anatomy, by means of machining with the usual laboratory mills.

5. Series of single use mandibular print holders for realizing directly final prints of the mandibular arch around the gingival crest (20) of edentulous patients, each mandibular print holder (16) comprising:
    a channel (17), which has a substantially horseshoe plan shape and an approximately U shaped cross section presenting a concave surface;

a lingual wall (18) which delimits the channel (17) from the internal side of the horseshoe and destined to be positioned in proximity to the tongue;

a labial wall (19) that delimits the channel (17) from the external side and destined to be positioned in proximity to the lower lip; the channel (17) and the walls (18,19) being realized in such a way as to surround the gingival crest (20) maintaining a certain gap (21) between the surface of the print holder (16) and the surface of the gum for the material for obtaining the prints;

a border (27) delimiting the labial wall (19) provided with lateral elevations (22), in the region between the third and the fifth tooth, a central incision (23) in correspondence with the central frenulum, two curvatures for the tuberosities of the chin situated to the side of the central incision (23);

an inner border (28) delimiting the lingual wall (18) provided with two incisions (29) situated between the fourth and the fifth tooth, and anteriorly in a central position presenting an incision (30) for the lingual frenulum;

characterized in that the channel (17) is provided with two rear tissue supports (25) having single situated in the premolar-molar region and an anterior central tissue support (31), the supports (25,31) having a large bearing surface and being raised areas of the concave surface of the channel (17) that bear down on patient's gums and prevent the print holder from swivelling and moving (16) when it is positioned on the patient and the movements of the mouth muscles are recorded and allow an adequate thickness of the material for obtaining the prints, and in that the mandibulary print holder is made of cold-polymerised polymethylmetacrylate, a rigid plastic material machinable with laboratory mills for eliminating any excess material for adapting the print holder to the patient's anatomical characteristics.

6. Series of print holders according to claim 5, characterized in that, in the outer rear-lateral part, the print holder (16) presents a recess (24) shaped like an inverted and elongated S.

7. Series of print holders according to claim 6, characterized in that in order to favor its positioning, the print holder (16) is provided with a straight handle (32) located centrally and anteriorly, and it is provided with two projections (33) whose purpose is to hold still the print holder (16) during the functional rimming process.

8. Series of print holders according to claim 5, characterized in that in order to favor its positioning, the print holder (16) is provided with a straight handle (32) located centrally and anteriorly, and it is provided with two projections (33) whose purpose is to hold still the print holder (16) during the functional rimming process.

* * * * *